United States Patent
Konrad (10) Patent No.: US 6,705,187 B2
(45) Date of Patent: Mar. 16, 2004

(54) DEVICE FOR STRETCHING CRYOSTATIC SECTIONS

(75) Inventor: Marc Konrad, Dossenheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 104 days.

(21) Appl. No.: 09/964,673

(22) Filed: Sep. 28, 2001

(65) Prior Publication Data

US 2002/0038590 A1 Apr. 4, 2002

(30) Foreign Application Priority Data

Sep. 29, 2000 (DE) .......................................... 100 48 724

(51) Int. Cl.[7] ............................................... B26D 7/01
(52) U.S. Cl. .............................. 83/13; 83/167; 83/915.5
(58) Field of Search ........................... 83/165, 195, 171, 83/175, 915.5, 167, 698.11, 13

(56) References Cited

U.S. PATENT DOCUMENTS

| 3,456,538 | A | * | 7/1969 | Barton et al. ................... 83/171 |
| 4,569,647 | A | * | 2/1986 | McCormick ................ 425/117 |
| 5,082,254 | A | * | 1/1992 | Hunnell et al. ............. 269/269 |
| 5,161,446 | A | * | 11/1992 | Holbl et al. ................... 83/703 |
| 5,535,654 | A | * | 7/1996 | Niesporek et al. ............. 83/364 |
| 5,551,326 | A | * | 9/1996 | Goodman ..................... 83/167 |
| 5,669,278 | A | * | 9/1997 | Metzner ....................... 83/165 |
| 5,812,312 | A | * | 9/1998 | Lorincz ........................ 359/397 |
| 6,000,309 | A | * | 12/1999 | Gnagi .......................... 83/167 |

FOREIGN PATENT DOCUMENTS

| DE | 25 06 255 | 9/1976 |
| DE | 20 28 898 | 7/1978 |

OTHER PUBLICATIONS

LEITZ Cryostat, Catalog No. 913 039, Ernst Leitz Wetzlar GmbH, Jul. 1982.

* cited by examiner

Primary Examiner—Allan N. Shoap
Assistant Examiner—Phong Nguyen
(74) Attorney, Agent, or Firm—Foley & Lardner (57) ABSTRACT

A device for stretching cryostatic sections includes a sectioning knife and a plate. The plate is arranged on a back side of the sectioning knife so that a gap for receiving the cryostatic section is formed between the back of the sectioning knife and the plate. A frame, open in a direction of an edge of the knife, is provided for receiving the plate. The frame has internally located shaped-on webs having support surfaces to support the plate, and a contact rim for setting the frame onto the back of the sectioning knife. A height difference between the contact rim and the support surfaces defines a dimension of the gap.

17 Claims, 7 Drawing Sheets

DEVICE FOR STRETCHING CRYOSTATIC SECTIONS

This invention claims priority of the German patent application 100 48 724.6 which is incorporated by reference herein.

FIELD OF THE INVENTION

The invention concerns a device for stretching cryostatic sections.

BACKGROUND OF THE INVENTION

In cryostats, thin sections of frozen specimens are produced with a microtome and are then mounted on a specimen slide and examined with a microscope. As the frozen specimens are sectioned, the difficulty exists that the frozen specimens curl up during sectioning. These curled-up specimens are very difficult to mount on a specimen slide, and the risk additionally exists of breaking the specimens. Section stretching devices are used to prevent the undesirable curling. These section stretchers have a glass or plexiglas plate that is arranged on the knife back, parallel to and at a short distance from the knife edge, in such a way that a thin gap is created between the knife back and the plate. During sectioning, the sectioned specimen slides into the gap between the plate and the knife back.

After sectioning, the section stretcher is taken off the knife back and the sectioned specimen is removed from the knife back. This removal is accomplished by the fact that a specimen slide, warmed to room temperature, is set on the knife edge and slowly lowered onto the sectioned specimen. Upon contact, the ice in the specimen abruptly thaws and the sectioned specimen adheres to the specimen slide.

DE 20 28 898 C3 discloses and describes a section stretcher of this kind in a cryostat. The plate of the section stretcher is arranged parallel to the knife back by way of a lever device having a motorized drive. The section stretcher is in this case a constituent of an automatic section removing system with specimen slides. The material of which the plate of the section stretcher is made and the manner in which the gap between the knife back and the plate of the section stretcher is formed are, however, left undefined in this document. The full disclosure of DE 20 28 898 C3 is hereby incorporated by reference.

DE 25 06 255 B2 discloses an ultramicrotome having a section stretcher in which the plate of the section stretcher is formed from the countermember of a broken triangular glass knife. Broken triangular glass knives are, however, used exclusively in ultramicrotomy and are unsuitable for larger specimens. The full disclosure of DE 25 06 255 B2 is hereby incorporated by reference.

The document "LEITZ 1720 Cryostat, catalog no. 913 039, Ernst Leitz Wetzlar GmbH, July 1982" depicts a cryostat having a section stretcher in which the plate of the section stretcher is configured as a one-piece injection-molded plexiglas plastic part having webs shaped onto both ends. The requisite gap between the plexiglas plate and the knife back is defined by the shaped-on webs. The webs shaped onto both ends are present in this case on both the front side and the rear side of the plexiglas plate, so the plate is usable from both sides. The use of plexiglas has the advantage that the component is easy to manufacture as an injection-molded part, and the finished part can moreover easily be machined by drilling, milling, and the like. It is disadvantageous, however, that the plastic part is easily scratched and that static charging takes place to a certain extent. The plexiglas moreover has poor chemical resistance. Since it is necessary to work with solvents in the vicinity of the sectioning knife for cleaning purposes, the risk exists that the plate will lose its transparency and thus become unusable. The full disclosure of this document is hereby incorporated by reference.

Section stretchers having glass plates are also known. Here the necessary webs are configured as glass strips and are mounted on the glass plate with a suitable adhesive. This method is very laborious, however, since the glass must be carefully cleaned before adhesive bonding. Since the gap between the knife back and plate is about 0.15 mm, the glass webs are correspondingly delicate and can easily break off when set onto the steel knife in the microtome. Glass webs of nonuniform thickness, however, result in an "oblique" gap between the knife and glass plate and are therefore unusable.

In a further development of these section stretchers, a multi-layer baked enamel has been applied onto the glass plate instead of the adhesively bonded glass webs. This has the disadvantage, however, that the permissible tolerance for the gap, which is approximately 0.15 mm in thickness, can only insufficiently be maintained. A further disadvantage lies in the fact that the hardened enamel is very brittle and thus, as in the case of the adhesively bonded glass strips, easily chips off when set onto the steel microtome knife.

SUMMARY OF THE INVENTION

It is therefore the object of the present invention, proceeding from the known existing art, to configure a section stretcher in a more robust fashion and also to ensure easy replaceability of the plate. These and other advantages will be clear to one skilled in the art.

The present invention provides for a device for stretching cryostatic sections, comprising: a sectioning knife; a plate arranged on a back side of the knife so that a gap for receiving the cryostatic section is formed between the plate and the back of the knife; a frame, open in a direction of an edge of the knife, for receiving the plate; and webs internally located and shaped on the frame and having support surfaces to support the plate, wherein the frame includes a contact rim for setting the frame onto the back of the knife, and wherein a height difference between the contact rim and the support surfaces defines a dimension of the gap. The frame may be of one-piece configuration, and its shape may be of a rectangle or a triangle. The plate may be made of glass or plastic, and may be detachably secured to the frame by two screws arranged on the frame. Further, the webs may be provided on at least two limbs of the frame.

DETAILED DESCRIPTION

Figure 1:
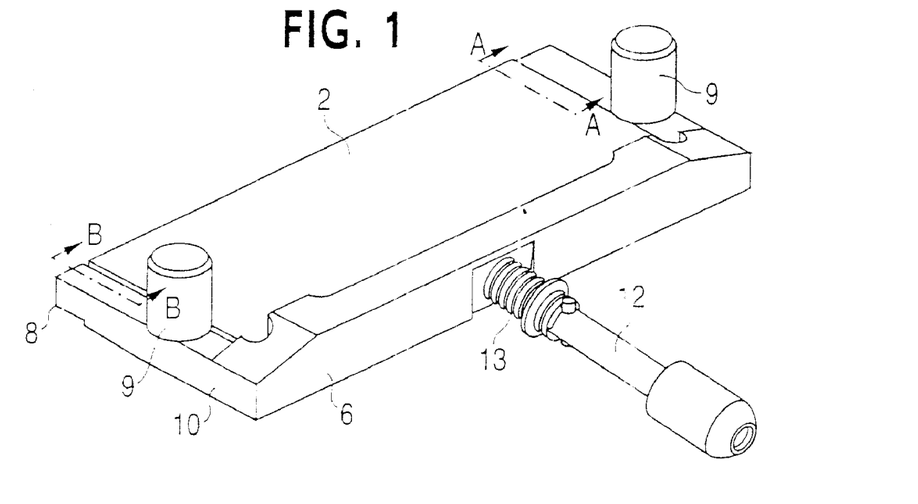
FIG. 1 shows a view of the section stretcher.

FIG. 1 shows a view of the section stretcher with a U-shaped frame 6 in whose inner receptacle a plate 2 is arranged. Plate 2 is secured in frame 6 detachably by way of two screws 9. Limbs 10 of frame 6 are configured with a contact rim 8 for the section stretcher to make contact against the back surface of a sectioning knife (not depicted). The section stretcher can be mounted, via a handle 12 having a compression spring 13, on a knife holder (not depicted) of a microtome.

Figure 2:
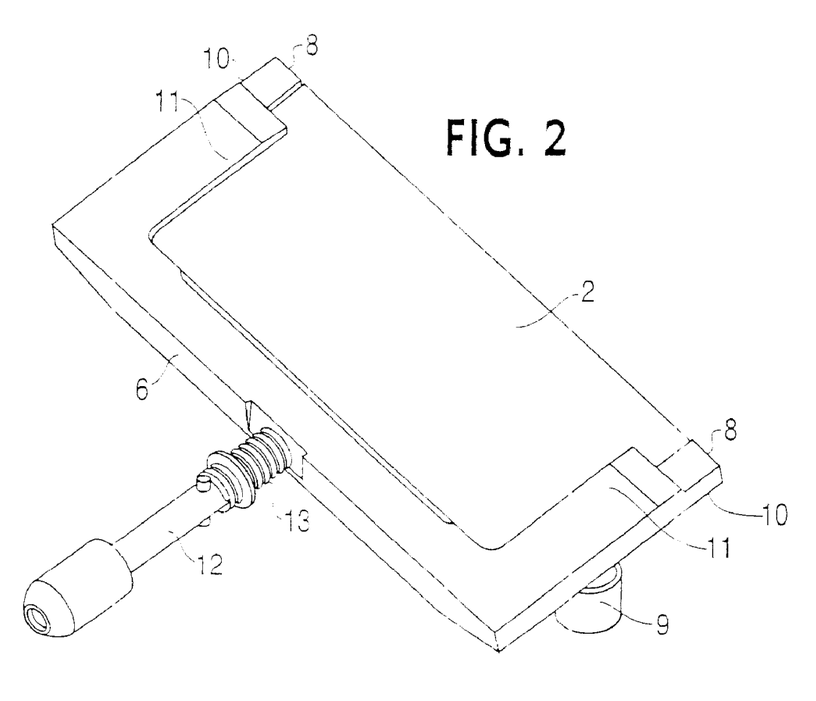
FIG. 2 shows the underside of the section stretcher.

FIG. 2 shows the underside of the section stretcher with shaped-on webs 11 and the two contact rims 8 provided on limbs 10. Webs 11 project into the interior of frame 8 and there form support surfaces for plate 2.

Figure 3:
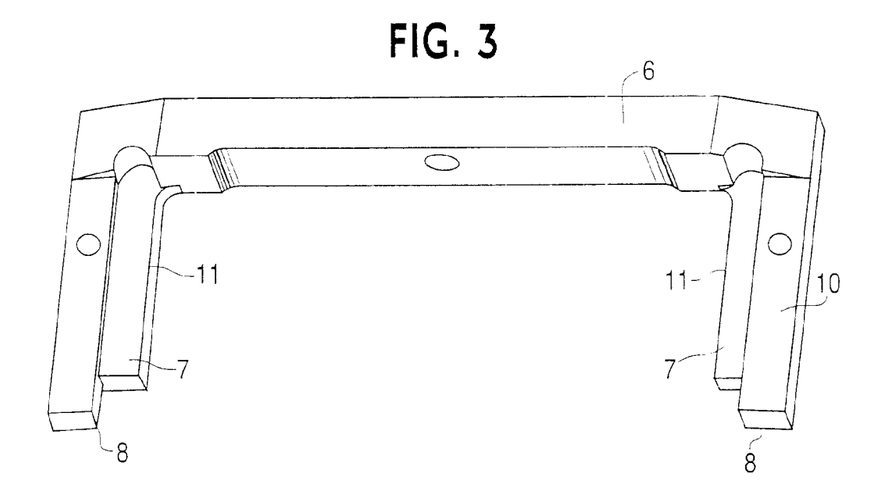
FIG. 3 shows a view of the frame.

FIG. 3 shows a view of frame 6 with the two limbs 10 and the shaped-on webs 11. Webs 11 are ground flat on their upper side and form support surfaces 7 for the plate. The difference in height between contact rim 8 and support surface 7 is the dimension of the gap.

Figure 4:
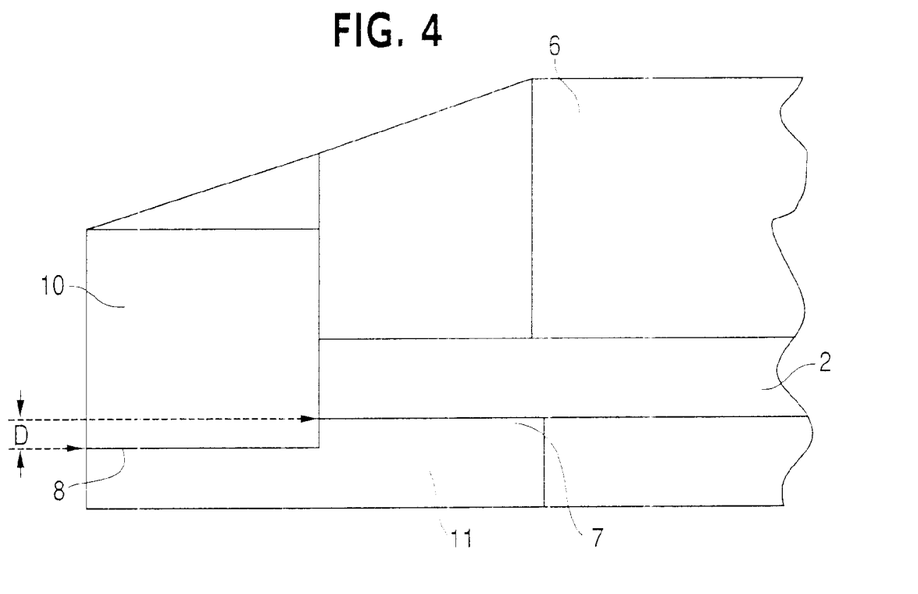
FIG. 4 shows a frontal view of the frame.
Figure 9:
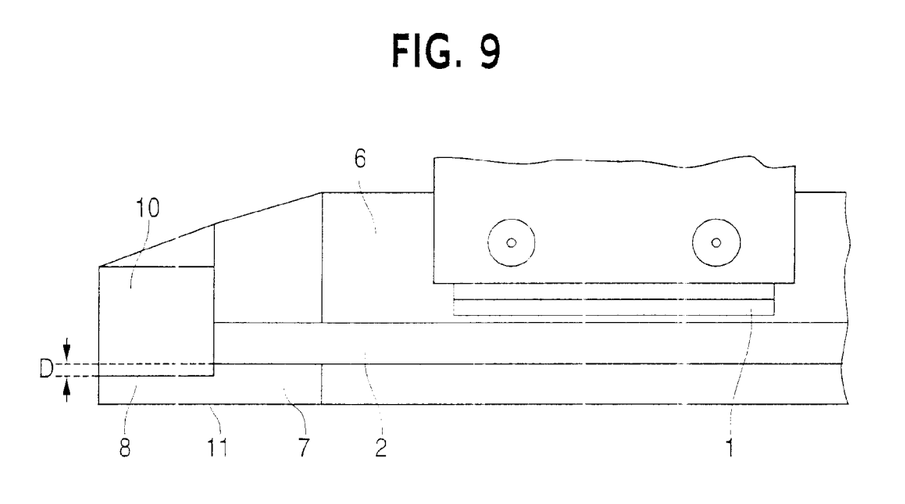
FIG. 9 shows a view of the spatial relationship of the knife 1, the plate 2, the gap formed by the contact rim 8, the support surface 7 and the frame 6.

FIG. 4 shows a frontal view of frame 6 with limbs 10 and the shaped-on web 11. This view clearly depicts the height difference D between contact rim 8 and support surface 7; support surface 7 for plate 2 lies in a different plane from contact rim 8. FIG. 9 shows an exemplary embodiment of a device for stretching cryostatic sections, showing a possible spatial relationship of the knife 1, the plate 2, the gap formed by the contact rim 8, the support surface 7 and the frame 6.

Figure 5:
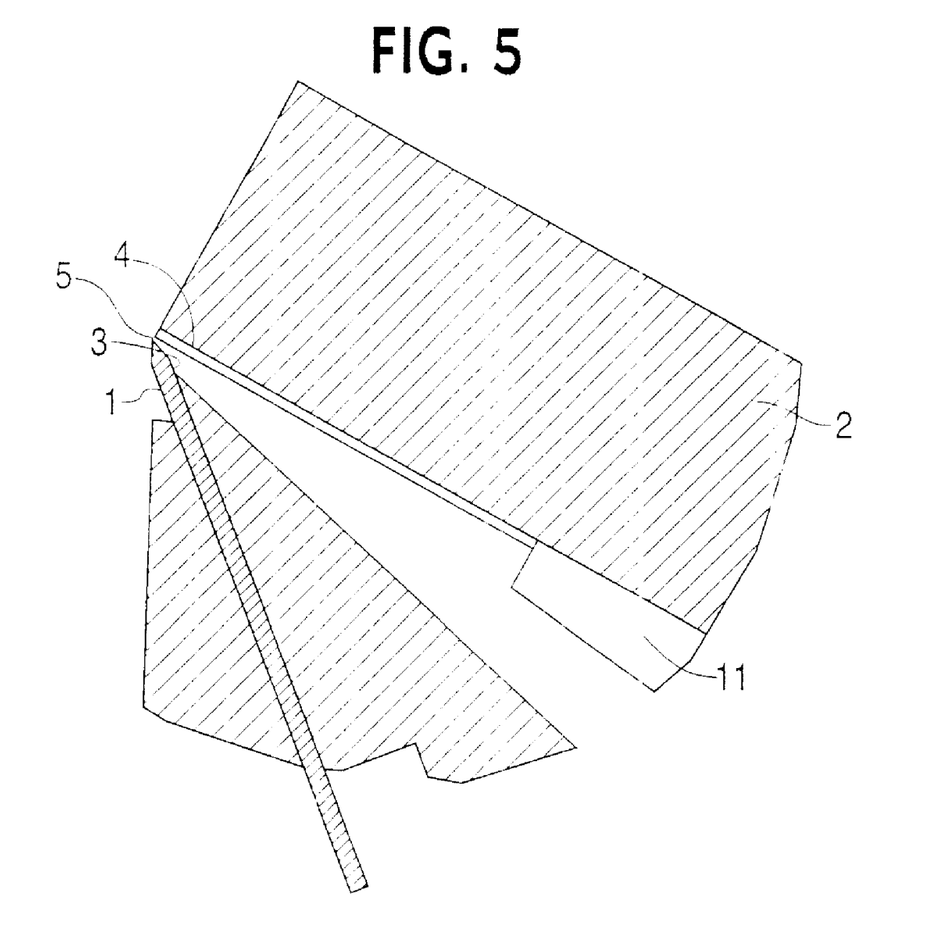
FIG. 5 shows a cross-sectional view of the section stretcher resting on the sectioning knife, the cross-sectional view of the section stretcher taken along section A—A of FIG. 1.

FIG. 5 is a sectioned depiction of the section stretcher resting on sectioning knife 1. The contact rim (not depicted here) rests on back surface 3 of sectioning knife 1 and forms gap 4 between the lower edge of plate 2 and back surface 3 of sectioning knife 1. The specimen pieces cut off by knife edge 5 are received in this gap 4.

Figure 6:
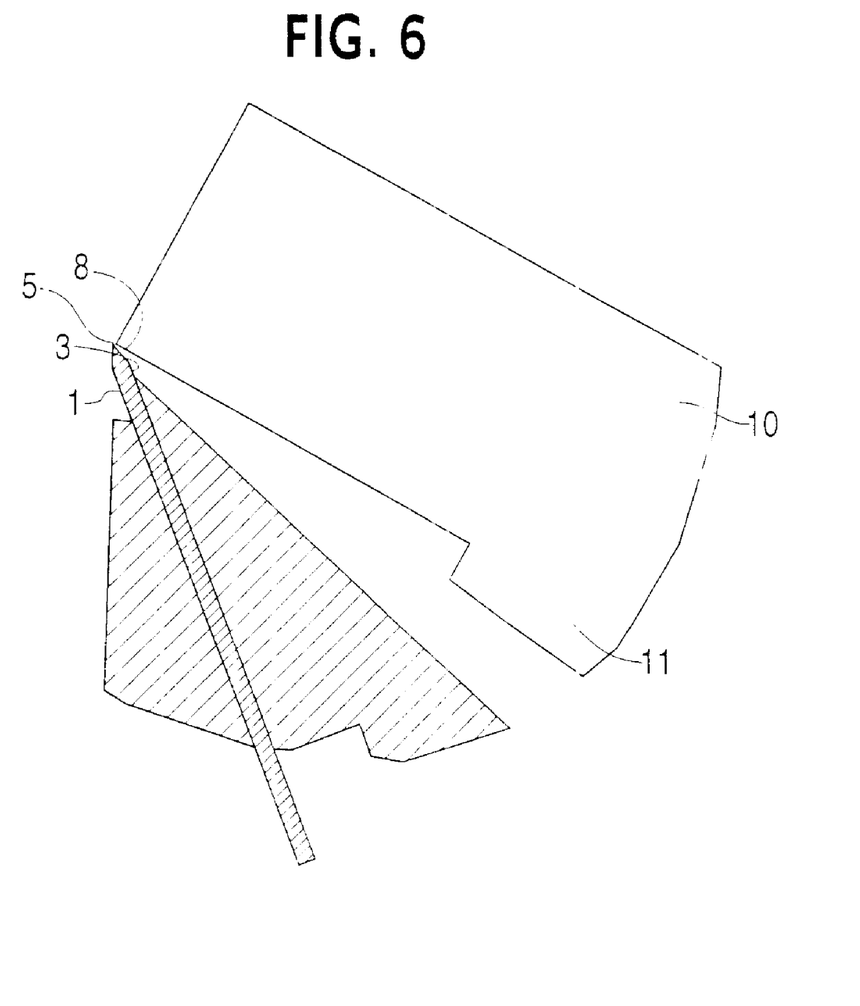
FIG. 6 shows a cross-sectional view of the section stretcher resting on the sectioning knife, the cross-sectional view of the section stretcher taken along section B—B of FIG. 1.

FIG. 6 shows a cross-sectional view of the section stretcher resting on the sectioning knife 1, the cross-sectional view of the section stretcher taken along section B—B of FIG. 1.

The device for stretching cryostatic sections is characterized in that a frame open toward one side is provided for reception of the plate, and the frame has internally located shaped-on webs. The webs are equipped with a support surface for the plate. The frame furthermore has a contact rim for setting the frame onto the back surface of the sectioning knife. The spacing between the contact rim and the support surface forms the defined gap for receiving the sectioned specimen. The result of this configuration of the section stretcher is that contact is no longer created between the delicate plate and the sectioning knife. The dimensions of the gap now are no longer dependent on the material properties of the plate, but are defined unequivocally by the spacings on the frame. It is therefore also possible to use plates of different material thicknesses without causing any change in the dimension for the gap.

The advantageous result of a one-piece configuration of the frame is that not only great stability but also high precision for the support surfaces and the contact rim are achieved. The surfaces and rims of the frame can be machined on a CNC machine tool in a single clamping.

Figure 7:
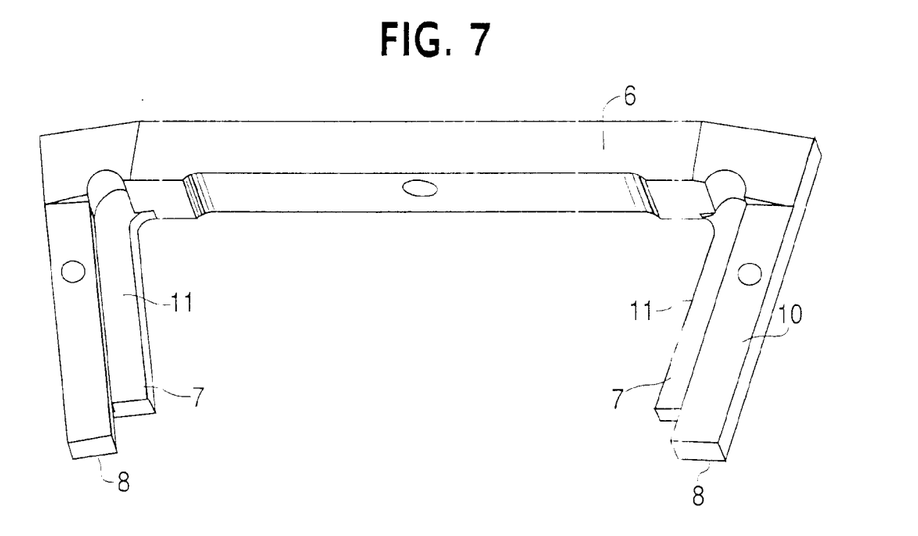
FIG. 7 shows a view of a second embodiment of the frame.
Figure 8:
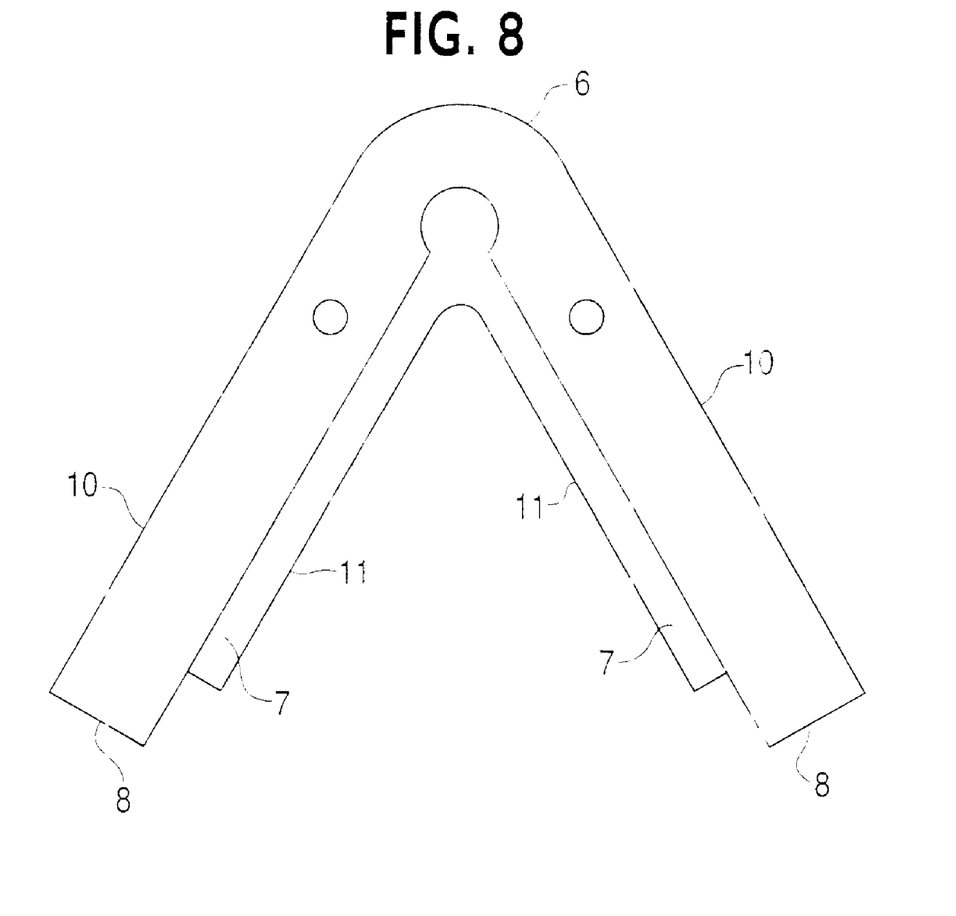
FIG. 8 shows a view of a third embodiment of the frame.

It has proven advantageous if the frame is configured as a U-shaped component. The frame can of course also, in the context of high mechanical stability, be produced as a triangle, as shown in FIGS. 7 and 8, or other shapes.

The plate, which is secured detachably in the frame via two screws, can be manufactured both from glass or from transparent plastic. Since contact is no longer created between the sectioning knife and the plate, the risk of damage is minimized. After loosening the two screws, the plate can easily be replaced with another plate. This manner of securing the plate in the frame means it is no longer necessary to provide additional holders or holes on the plate.

The webs that are shaped onto the limbs of the frame can extend internally continuously around the frame. This has the advantage that a large support surface is formed for the plate. For large frames and very thin plates, the risk of breakage can thus be decreased. It may, however, also be sufficient if the webs are provided on only two limbs of the frame, or if the webs are shaped onto the frame in the manner of a three-point support.

The invention has been described in detail with particular reference to certain preferred embodiments thereof, but it will be understood that variations and modifications can be effected within the spirit and scope of the invention.

What is claimed is:

1. A device for stretching cryostatic sections, comprising:
   a sectioning knife;
   a plate arranged on a back side of the knife so that a gap adapted to receive the cryostatic section is formed between the plate and the back of the knife;
   a frame, open in a direction of an edge of the knife, adapted to receive the plate; and
   webs internally located and shaped on the frame and having support surfaces to support the plate,
   wherein the frame includes a contact rim adapted to set the frame onto the back of the knife, and
   wherein a height difference between the contact rim and the support surfaces defines a dimension of the gap.

2. The device for stretching cryostatic sections as defined in claim 1, wherein the frame is of one-piece configuration.

3. The device for stretching cryostatic sections as defined in claim 1, wherein a shape of the frame is one of a rectangle and a triangle.

4. The device for stretching cryostatic sections as defined in claim 1, wherein the plate is made of one of glass and plastic.

5. The device for stretching cryostatic sections as defined in claim 1, wherein the plate is detachably secured to the frame by at least two fasteners arranged on the frame.

6. The device for stretching cryostatic sections as defined in claim 1, wherein the webs are provided on at least two limbs of the frame.

7. The device for stretching cryostatic sections as defined in claim 1, wherein the frame has side walls that abut side walls of the plate on at least two sides of the plate, the side walls of the plate being parallel to the thickness direction of the plate.

8. The device for stretching cryostatic sections as defined in claim 1, wherein the sectioning knife does not contact the plate.

9. The device for stretching cryostatic sections as defined in claim 1, wherein the distance between the sectioning knife and the plate is independent of the thickness of the plate.

10. The device for stretching cryostatic sections as defined in claim 1, wherein the distance between the sectioning knife and the plate is the same for a plurality of plates having different thickness.

11. A device for stretching cryostatic sections, comprising:
- a frame adapted to receive a plate, the plate being arranged on a back side of a knife so that a gap adapted to receive the cryostatic section is formed between the plate and the back of the knife, the frame being open in a direction of an edge of the knife; and
- webs internally located and shaped on the frame and having support surfaces to support the plate,
- wherein the frame includes a contact rim adapted to set the frame onto the back of the knife, and
- wherein a height difference between the contact rim and the support surfaces defines a dimension of the gap.

12. The device for stretching cryostatic sections as defined in claim 11, wherein the frame has side walls that abut side walls of the plate on at least two sides of the plate, the side walls of the plate being parallel to the thickness direction of the plate.

13. The device for stretching cryostatic sections as defined in claim 11, wherein the knife does not contact the plate.

14. The device for stretching cryostatic sections as defined in claim 11, wherein the distance between the knife and the plate is independent of the thickness of the plate.

15. The device for stretching cryostatic sections as defined in claim 11, wherein the distance between the sectioning knife and the plate is the same for a plurality of plates having different thickness.

16. A method for stretching cryostatic sections, comprising the following steps:
- obtaining a plate and a frame adapted to receive the plate and receiving the plate in the frame, the frame having webs internally located and shaped on the frame and having support surfaces to support the plate, wherein the frame includes a contact rim adapted to set the frame onto a back side of a knife; and
- setting the frame in conjunction with the plate on the back side of the knife so that:
  - a gap adapted to receive the cryostatic section is formed between the plate and the back of the knife;
  - the contact rim rests on the back surface of the knife;
  - a height difference between the contact rim and the support surfaces defines a dimension of the gap; and
  - the frame is open in a direction of an edge of the knife.

17. The method for stretching cryostatic sections as defined in claim 16, further comprising using a plurality of plates having different thickness, wherein the distance between the knife and the plate is, excluding dimensional tolerancing and manufacturing defects, exactly the same for the plurality of plates having different thickness.

* * * * *